United States Patent [19]

Fujiwara et al.

[11] Patent Number: 4,786,162
[45] Date of Patent: Nov. 22, 1988

[54] RETINAL CAMERA

[75] Inventors: Hiroshi Fujiwara, Hachiouji; Kazuyuki Minami, Musashino, both of Japan

[73] Assignee: Olympus Opitical Co., Ltd., Tokyo, Japan

[21] Appl. No.: 942,826

[22] Filed: Dec. 17, 1986

[30] Foreign Application Priority Data

Dec. 20, 1985 [JP] Japan .................. 60-287400

[51] Int. Cl.$^4$ .......................... A61B 3/14; G03B 7/00
[52] U.S. Cl. .................................. 351/206; 354/410
[58] Field of Search .............. 351/206, 221, 208; 354/432, 412, 62

[56] References Cited

U.S. PATENT DOCUMENTS 4,265,518 5/1981 Matsumura ............... 351/206
4,486,080 12/1984 Itoh et al. ................. 351/206
4,690,525 9/1987 Kobayashi et al. ....... 351/206

FOREIGN PATENT DOCUMENTS

52-69617 6/1977 Japan .
57-183830 11/1982 Japan .

Primary Examiner—Rodney B. Bovernick
Assistant Examiner—Paul M. Dzierzynski
Attorney, Agent, or Firm—Cushman, Darby & Cushman

[57] ABSTRACT

To make it possible to simply and positively estimate on the spot the quality of the retinal photographing result, a retinal camera provided with an automatic exposure controlling device, an estimate reference signal generating means, a quality estimating means estimating the quality of the photographing result and an estimation indicating means indicating the estimation result. The automatic exposure controlling device comprises an integrator integrating the output from a light receiving element, a keyboard putting in exposure conditions, an exposure data signal generating means, a reference voltage generating means, a comparative calculating means and a flash light emission controlling means.

15 Claims, 5 Drawing Sheets

RETINAL CAMERA

BACKGROUND OF THE INVENTION (a) Field of the invention:

This invention relates to a retinal camera adapted to a group examination.

(b) Description of the prior art:

The advent of a highly aged society is recently anticipated and the importance of an ophthalmoscopy which is effective to the medical examination and diagnosis of high age diseases tends to increase year by year. Under such circumstances, the demand for a retinal camera easily photographing retinal images in a collective medical examination is conspicuous. Generally, when photographing retinal images with a retinal camera in a collective medical examination, it is usual to use 35 mm-films in view of the necessity that retinal images of many persons must be photographed and the fact that clear photographs can be taken. However, only after the 35 mm-film is developed and enlarged, that is after the collective medical examination, will it be known whether the retinal image is properly photographed or not. Thus, this is typically known only several days after the medical examination ends. In case the photographing fails, the examinee must be called on again or must come to the medical establishment, causing much trouble and waste of time.

As one of the solutions of such problems, conventionally, as shown in Japanese Preliminary Patent Publication No. Sho 52-69617, a means for sensing whether the examinee has opened or closed their eyelid is provided, so that whether the eyelid is opened or closed can be indicated. When the eyelid is closed, the photographing means will be made inoperative to avoid any failure of photographing when the eyelid of the examinee is closed.

As another conventional example, as shown, for example, in Japanese Preliminary Patent Publication No. Sho 57-183830, a retinal camera having an image pickup means also include a photographing light branching means on a photographing light path. This allows at least a part of the photographing light to be led to the image pickup means. This photographing light is indicative of the retinal image recorded on the film, and may be indicated on such means as, for example, a monitor on the basis of the output of the image pickup means and whether a flare or the like is mixed in or not may be confirmed on the spot.

However, in the retinal camera shown in the above-mentioned Japanese Preliminary Patent Publication No. Sho 52-69617, an estimate must be made on the basis of whether the reflected light amount from the examined eye abnormally increases or not, and therefore a photographing failure will be unavoidable when the eye of the examinee moves momentarily, the center of the pupil and the optical axis of the photographing system are displaced from each other and the reflected light from the examined eye reduces. The retinal camera shown in the above-mentioned Japanese Preliminary Patent Publication No. Sho 57-183830 is a positive means by which the same as the photographed image can be observed but requires an image pickup tube for visible light only to confirm retinal images to be photographed, requires an image pickup tube for a visible light also in the case of an observing system with an infrared ray illumination and thus has a defect in that the retinal camera is made expensive and large.

SUMMARY OF THE INVENTION

A primary object of the present invention is to provide a retinal camera wherein, by adding a simple cheap electric circuit means, whether the photographed result is good or not can be estimated on the spot.

Another object of the present invention is to provide a retinal camera whereby retinal images of many examinees in a collective medical examination can be photographed positively and efficiently.

Figure 1:
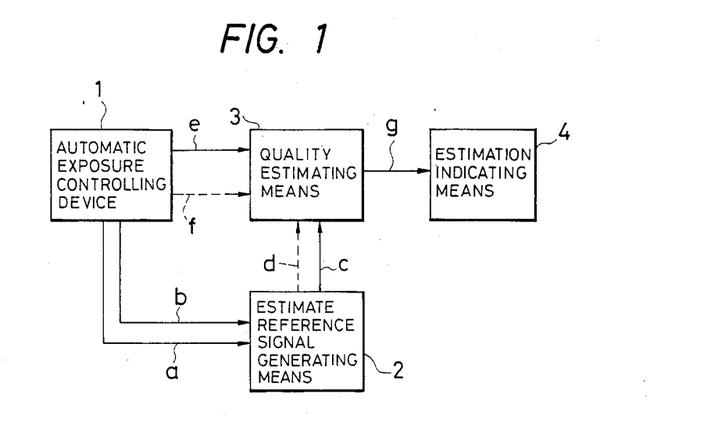
FIG. 1 is a conception diagram of a device for estimating a photographing quality of a retinal camera according to the present invention.

In the retinal camera according to the present invention, as shown in FIG. 1, within an automatic exposure controlling device or a so-called automatic electronic flash controlling device 1 which is provided in a general retinal camera so that a flash light may be projected onto an object to be photographed, its reflected light may be received by a light receiving circuit and, when the received light amount reaches a predetermined light amount, the flash light emission will be stopped, on the basis of an exposure data signal a and flash light emitting signal b, in an estimate reference signal generating means 2, estimate reference signals c or c and d are generated, in a quality estimating means 3, the quality of the photographing result is estimated from the time coincidence or size relation of a flash light stopping signal e within the above-mentioned automatic electronic flash controlling device 1 or an integrator output f and the above-mentioned estimate reference signal c or c and d, its estimate signal g is generated and on the basis of the estimate signal g and, in an estimation indicating means 4, the quality of the photographing result is made known to the examinee.

These and other objects as well as the features and advantages of the present invention will be apparent from the following detailed description of the preferred embodiments when taken in conjunction with the accompanying drawings.

DESCRIPTION OF THE PREFERRED EMBODIMENT

Figure 2:
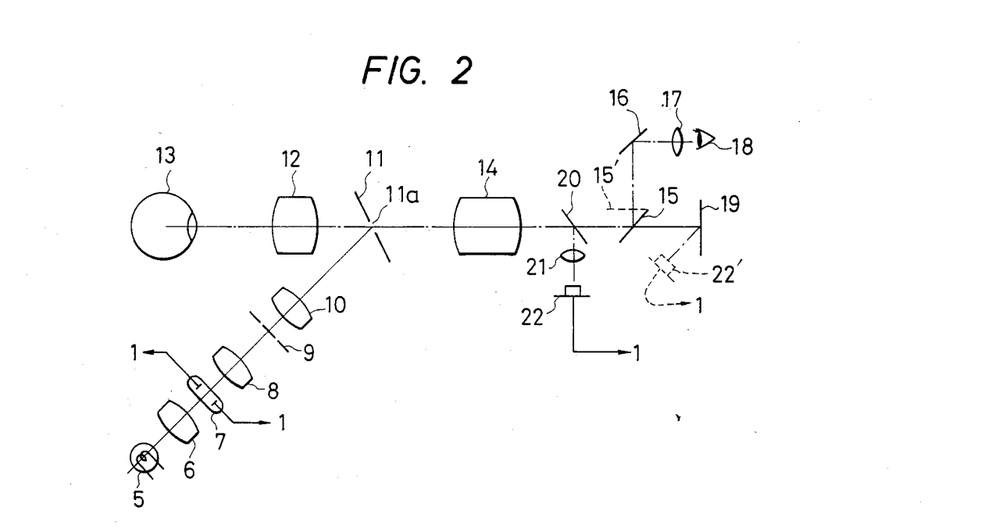
FIG. 2 is a view showing an optical system of an embodiment of a retinal camera according to the present invention.

The present invention shall be explained in detail in the following, on the basis of an illustrated embodiment. FIG. 2 is a view showing an optical system in which the present invention is applied to a mydriasis retinal camera. An illuminating system is formed of an observing light source 5 consisting, for example, of a halogen lamp, condenser lens 6, strobe tube 7 which is a photographing light source, relay lens 8, ring-shaped aperture stop 9, relay lens 10 and reflector 11 having an aperture 11a in the central part. The strobe tube 7 is electrically connected to the automatic electronic flash controlling device 1. An illuminating light emitted from the observing light source 5 or strobe tube 7 passes through the relay lens 8, ring-shaped aperture stop 9 and relay lens 10, is reflected by the reflector 11, passes through an objective 12 and illuminates a retina of an eye 13 to be examined. An observing system is formed of the objective 12, an image forming lens 14, reflector 15 capable of springing up, reflector 16 and eyepiece 17. A light emitted from the retina of the eye 13 passes through the objective 12, aperture 11a of the reflector 11 and image forming lens 14, is reflected by the reflectors 15 and 16, passes through the eyepiece 17 and enters an eye of an examiner. A photographing system is formed of the objective 12 in the rear of the reflector 15 capable of springing and a film 19 provided in a position conjugate with the retina of the eye 13 to be examined with respect to the image forming lens 14. At the time of photographing, a springing reflector 15 springs up to be in a position 15', therefore the light from the retina enters the film 19 and an image of the retina of the eye 13 being examined is formed. A light measuring system in photographing consists of a beam splitter 20 provided between the image forming lens 14 and springing reflector 15 and a relay lens 21 and light receiving element 22 provided on the reflected optical axis of the beam splitter 20. The light receiving element 22 is electrically connected with the automatic electronic flash controlling device 1. At the time of photographing, a part of the photographing light is taken out of the beam splitter and an electric signal (light amount signal) h proportional to the size of the light amount is generated in the light receiving element. The light amount signal h is transmitted to the automatic electronic flash controlling device 1 and the light emitting time of the strobe tube 7 is controlled by the automatic electronic flash controlling device 1 so that the exposure may be proper on the basis of the light amount signal h. As the light measuring system, instead of providing the beam splitter 20, relay lens 21 and light receiving element 22, as shown by the broken line in FIG. 2, a light receiving element 22' may be provided as directed to the light receiving surface of the film 19 so that the light may be measured on the film surface.

Figure 3:
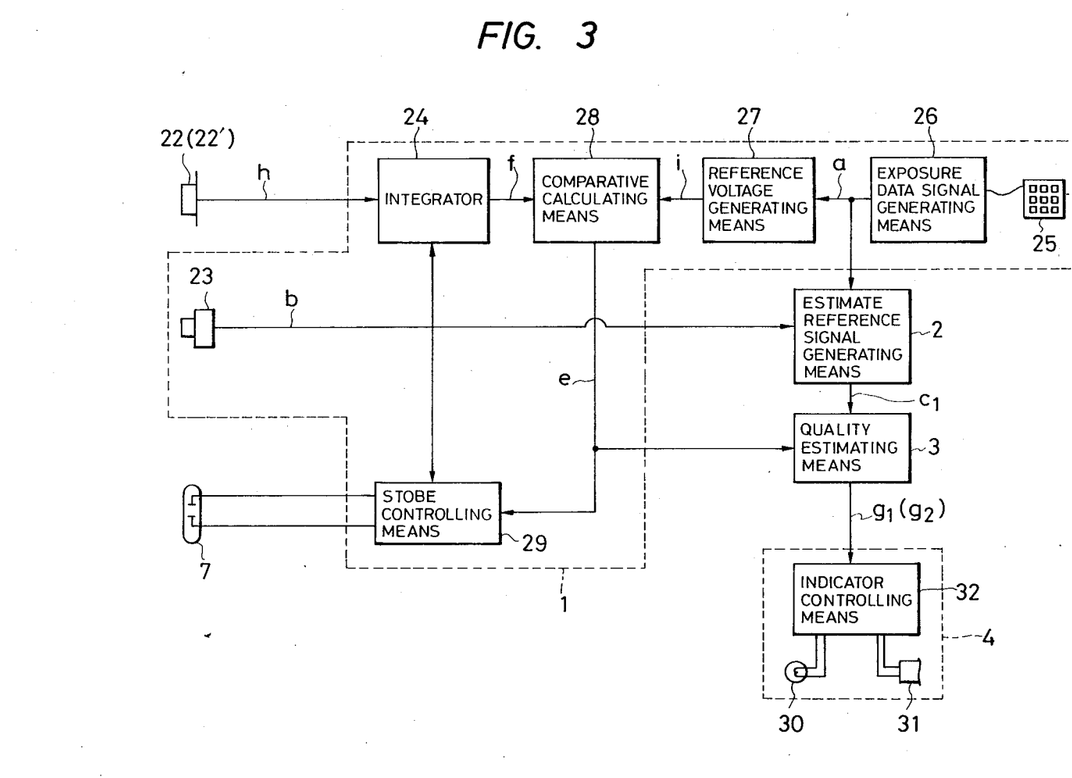
FIG. 3 is a block diagram of an electric circuit means of a first embodiment of a photographing quality estimating device to be used together with the optical system of FIG. 2.

FIG. 3 shows a block diagram of an electric circuit of a photographing quality estimating device of this embodiment. The automatic electronic flash controlling device 1 is formed of a photographing button 23 emitting a flash light emitting signal b, an integrator 24 initiating the integration of the light amount signal h by the flash light emitting signal b and generating the resultant integrator output f, a keyboard 25 putting in exposure conditions, an exposure data signal generating means 26 converting the exposure conditions input in from the keyboard 25 to an exposure data signal a and outputting this signal, a reference voltage generating means 27 putting out an exposure reference voltage i on the basis of the exposure data signal a, a comparative calculating means 28 outputting a flash light stopping signal e on the basis of the integrator output f and exposure reference voltage i and a strobe controlling means 29 emitting a light by flowing an electric current to the strobe tube 7 by the flash light emitting signal b, cutting of the current to the strobe tube 7 by the flash light stopping signal e and stopping the light emission of the strobe tube 7. At the time of photographing, if the sensitivity and the like of the film to be used are input by the keyboard 25, the exposure data signal a (digital signal) will be put out of the exposure data signal generating means 26. The reference voltage generating means 27 puts out an output voltage, that is, exposure reference voltage i corresponding to the exposure data signal a among several output voltages set in advance.

Figure 4:
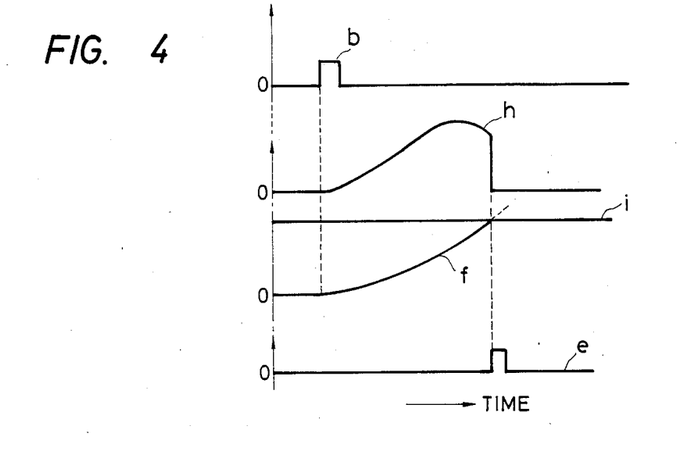
FIG. 4 is a time chart showing a principle of generating a flash light stopping signal of the estimating device shown in FIG. 3.

The electric circuit shall be explained in the following together with the time chart in FIG. 4. When the photographing button 23 is pushed, the flash light emitting signal b is output, its integrator 24 starts the operation by the flash light emitting signal b and, at the same time, the strobe controlling means 29 starts the light emission of the strobe tube 7 by the flash light emitting signal b. A part of the photographing light reflected by the retina of the eye being examined and coming into the photographing system enters the light receiving element 22, the light receiving element 22 generates such light amount signal h as in FIG. 4, the light amount signal h is integrated by the integrator 24 and the integrator 24 generates such integrator output f as in FIG. 4. The integrator output f is proportional to the total exposure amount to the film 19. The comparative calculating means 28 compares the integrator output f with the exposure reference voltage i and outputs the flash light stopping signal e at the time point when the integrator output f reaches the exposure reference voltage i as in FIG. 4. The strobe controlling means 29 stops the light emission of the strobe tube 7 by the flash light stopping signal e so that the exposure to the film 19 stops and the photographing is completed.

Figure 5:
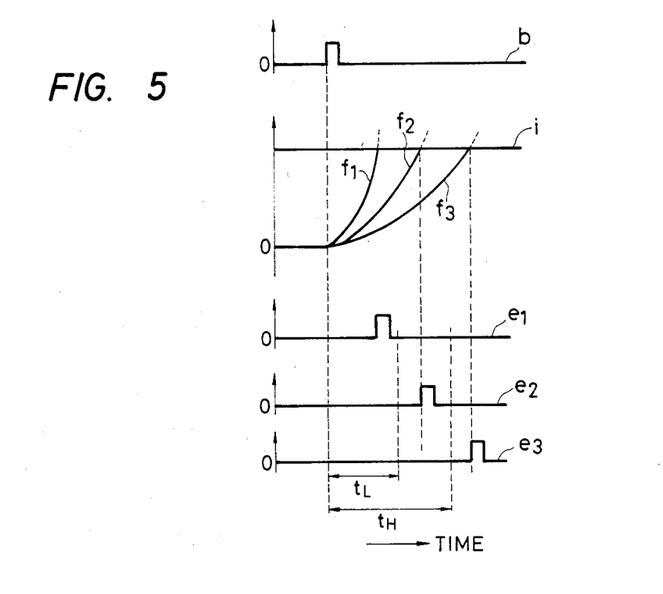
FIG. 5 is a time chart showing an estimating principle of the estimating device shown in FIG. 3.

In case the examinee blinks, the reflected light amount from the eyelid will be larger than from the retina. Therefore, as shown in FIG. 5, the integrator output $f_1$ when the eyelid is closed will rise up earlier than the integrator output $f_2$ when the retina is normally photographed. As a result, the flash light stopping signal $e_1$ which is produced when the eyelid is closed is output earlier than the flash light stopping signal $e_2$ produced when the retina is normally photographed. When the eye 13 being examined is not present in the photographing position, the photographing light amount will be smaller. Therefore, the integrator output $f_3$ when eye 13 being examined is not present will rise up later than the integrator output $f_2$ produced when the retina is normally photographed. As a result, the flash light stopping signal $e_3$ produced when the eye being examined is not present, will be output later than the flash light stopping signal $e_2$ produced when the retina is normally photographed. Therefore, if the flash light emission lasting time is between the lower limit value $t_L$ and upper limit value $t_H$ of a flash light emission lasting time representing a condition when the retina is normally photographed, the photographing result can be estimated to be good.

A photographing quality estimating device is formed of an estimate reference generating means 2 whereby the lower limit value $t_L$ (for example, 200 μs) and the upper limit value $t_H$ (for example, 3ms) are determined on the basis of the exposure data signal a, in the time $t_L$ after the flash light emission signal b is put in, the gate signal $c_1$ is switched from the low level to the high level and, in the time $t_H$ after the flash light emission signal b is put in, the gate signal $c_1$ is switched from the high level to the low level, a quality estimating means whereby an AND circuit is provided within, when the gate signal $c_1$ is on the high level, in case the flash light stopping signal e is put in, a pulse on the high level will be put out as a signal $g_1$ estimating the photographing result to be good and, when the gate signal $c_1$ is on the low level, in case the flash light stopping signal e is put in, a pulse on the low level will be put out as a signal $g_2$ estimating the photographing result to be not good, an indicator controlling means 32 whereby, in case the signal $g_1$ estimating the photographing result to be good is put in, a lamp 30 will be flickered and, in case the signal $g_2$ estimating the photographing result to be not good is put in, a buzzer 31 will be sounded and the lamp 30 and buzzer 31 electrically connected to the indicator controlling means 32.

The operation of this embodiment shall be explained in the following.

Figure 6:
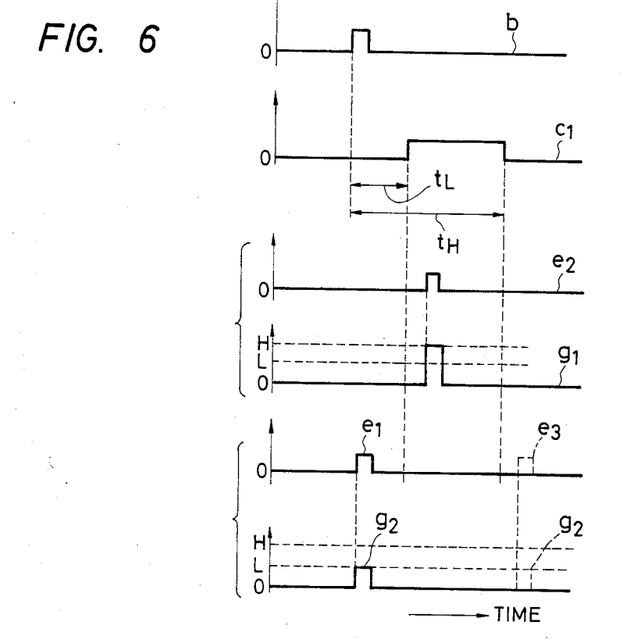
FIG. 6 is a time chart showing an actual estimating process of the estimating device shown in FIG. 3.

First of all, before photographing, the ASA sensitivity of the film to be used and exposure correcting values are input to the keyboard 25. The input data are converted to the exposure data signal a by the exposure data signal generating means 26 as described above and the exposure data signal a is put out. The exposure data signal a is put into the reference voltage generating means 27 and also into the estimate reference signal generating means 2 and the lower limit value $t_L$ and upper limit value $t_H$ of the flash light emission lasting time when the retina is normally photographed are calculated and set on the gasis of the exposure data. When the photographing button 23 is pushed, photographing will be made by the automatic electronic flash controlling device as described above. The flash light emitting signal b from the photographing button 23 is put also into the estimate reference signal generating means 2 and the gate signal $c_1$ as in FIG. 6 is generated according to the above-mentioned lower limit value $t_L$ and upper limit value $t_H$. The gate signal $c_1$ is put into the quality estimating means 3. When the gate signal $c_1$ is on the high level, in case the flash light stopping signal e is put in, the photographing result will be estimated to be good. Therefore, as in FIG. 6, if the flash light stopping signal $e_2$ when the retina is normally photographed is put in, the signal $g_1$ estimating the photographing result to be good and consisting of a pulse signal on the high level will be put out. On the other hand, as the flash light stopping signals $e_1$ and $e_2$ respectively when the eyelid is closed and when the eye being examined is not present are put in when the gate signal $c_1$ is on the lower level, the signal $g_2$ estimating the photographing result to be not good and consisting of a pulse signal on the low level will be put out. The estimating signal g is put into the indicator controlling means 32 of the estimation indicating means 4. The indicator controlling means 32 will make it known to the examiner that the photographing result is good by flickering the lamp 30 when the signal $g_1$ estimating the photographing result to be good comes in and that the photographing result is not good by sounding the buzzer 31 when the signal $g_2$ estimating the photographing result to be not good comes in.

As in the above, the retinal camera according to the present invention can make the quality of the photographing result known to the examiner by only adding a simple cheap circuit to a conventional retinal camera.

Figure 7:
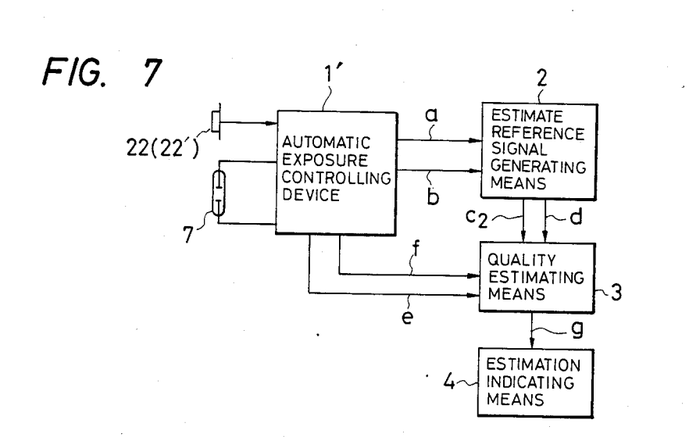
FIG. 7 is a block diagram of an electric circuit means of a second embodiment of the photographing quality estimating device to be used together with the optical system of FIG. 2.
Figure 8:
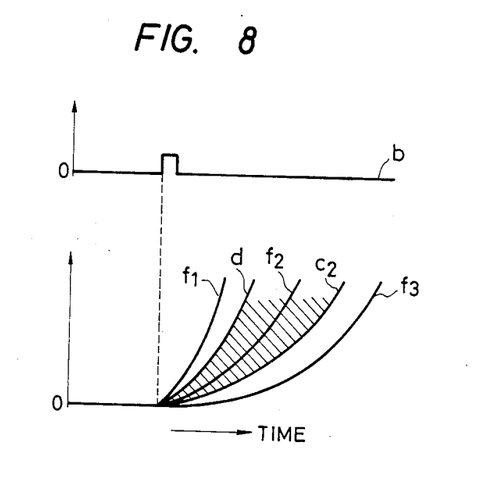
FIG. 8 is a graph showing an estimating principle of an estimating device of the second embodiment.

Now, a block diagram of an electric circuit of the photographing quality estimating device of the second embodiment is shown in FIG. 7 and a time chart is shown in FIG. 8. This estimating device is formed of an estimate reference signal generating means 2 whereby a lower limit value $c_2$ and upper limit value d of the rising rate of the integrator output f when the retina is normally photographed are determined as in FIG. 8 on the basis of the exposure data signal a from an automatic exposure controlling device 1' and outputs corresponding respectively to the lower limit value $c_2$ and upper limit value d of the rising rate of the integrator output f when the retina is normally photographed are issued by the input of the flash light emitting signal b, a quality estimating means 3 whereby a value f of the rising rate of the integrator output from the automatic exposure controlling device 1' determined at a predetermined time point is compared with the lower limit value $c_2$ and upper limit value d of the integrator output when the retina is normally photographed and, in case $f>d$ or $f<c_2$ until the flash light stopping signal e is put in, the signal $g_2$ estimating the photographing result to be not good will be put out and, in case the relation of $c_2 \leq f \leq d$ is kept until the flash light stopping signal e is put in, the signal $g_1$ estimating the photographing result to be good will be put out and an estimation indicating means 4 whereby the quality of the photographing result is made known to the examiner by the lamp, buzzer or announcement according to the estimating signal g from the quality estimating means 3. The above-mentioned value f of the rising rate can be determined by obtaining the difference ($\Delta i = i_2 - i_1$) between the voltage value $i_1$ of the integrator output at the time $t_1 = 150$ μs and the voltage value $i_2$ of the integrator output at the time $t_2 = 160$ μs and calculating $f = k\Delta i$ (k: constant) if the aforesaid lower limit value $t_L = 200$ μs is adopted.

The operation of the second embodiment shall be explained in the following.

First of all, the exposure data signal a from the automatic exposure controlling device 1' is put into the estimate reference signal generating means 2. By the estimate reference signal generating means 2, the rising rates of the lower limit value $c_2$ and upper limit value d of the rising rate of the intregator output f when the retina is normally photographed as shown in FIG. 8 are determined on the basis of the exposure data signal a. In case the retina is normally photographed, the lower limit value $c_2$ and upper limit value d will be always so set that the value $f_2$ of the rising rate of the integrator output may be $c_2 \leq f_2 \leq d$, that is, within the hatched portion shown in FIG. 8. When a photographing button not illustrated in pushed, photographing will be started by the automatic exposure controlling device 1' as described above. At the same time, the flash light emitting signal b from the photographing button is put into the estimate reference signal generating means 2. By the estimate reference signal generating means 2, the outputs corresponding respectively to the lower limit value $c_2$ and upper limit value d of the rising rate of the integrator output f when the retina is normally photographed are generated by the input of the flash light emitting signal b. The value f of the rising rate of the integrator output from the automatic exposure controlling device 1' and the outputs $c_2$ and d from the estimate reference signal generating means 2 are put into the quality estimating means 3. By the quality estimating means 3, the value of the rising rate of the integrator output is compared with the lower limit value $c_2$ and upper limit value d of the rising rate of the integrator output when the retina is normally photographed. As in FIG. 8, the value $f_2$ of the rising rate of the integrator output when the retina is normally photographed satisfies $c \leq f_2 \leq d$. That is to say, as the value $f_2$ is within the hatched portion, as soon as the flash light stopping signal $e_2$ is put in, the signal $g_1$ estimating the photographing result to be good will be put out. When the eyelid is closed and in case the eye to be examined is not present, the values $f_1$ and $f_3$ will be out of the hatched portion and therefore, at the time point when they come out of the hatch portion, the signal $g_2$ estimating the photographing result to be not good will be put out. By the estimation indicating means 4, on the basis of the estimating signal g from the quality estimating means 3, the quality of the photographing result can be made known to the examiner by the lamp, buzzer or announcement.

This second embodiment has the following advantages. As the rising rate of the integrator output is used as the parameter to estimate the quality of the exposure, the estimation result can be obtained when a predetermined time has passed after the flash light emission. Thus, the quality of the estimation result can be obtained earlier than the lower limit value $t_L$ (200 μs under a certain condition) of the first embodiment. Therefore, in case the estimation result is not good, a warning can be issued at the earlier time point to stop the flash light emission. Therefore, there are advantages that the second embodiment can be realized by only adding a simple circuit and can more accurately estimate the quality of the photographing result by eliminating the defect of the above-mentioned first embodiment.

An example of applying the present invention to a mydriasis retinal camera has been shown in the above. It is needless to say that the present invention can be applied also to a non-mydriasis retinal camera. In a non-mydriasis camera, it is general to make an observation with a monitor. Therefore, a means whereby a monitor is commonly used for the estimation indicating means 4 and the estimation result is indicated on the monitor is naturally possible from the known technique. The above-mentioned second embodiment is very effective particularly to a non-mydriasis retinal camera, because, as the flash light emission is stopped in the step where abnormal photographing is sensed, in such case of photographing without using any mydriasis agent as in the non-mydriasis camera, the pupil contraction of the examinee can be controlled to be minimum, thereby the time until the pupil of the examinee opens to be of a size large enough for rephotographing can be reduced and the time loss until the re-photographing can be controlled to be minimum.

As described above, in the retinal camera according to the present invention, the quality of the photographing result can be known on the spot by only adding a simple cheap circuit device and therefore there are advantages that the anxiety about the quality of the photographing result can be eliminated, re-photographing can be easily judged just after photographing and particularly, in the conventional retinal photographing at the time of the collective medical examination requiring much trouble and time in re-photographing in days after photographing, the retinal photograph of any examinee can be positively kept, the above-mentioned trouble and time can be omitted and the collective medical examination activity can be made easy and active.

What is claimed is:

1. A retinal camera comprising:
   automatic exposure controlling means for emitting a flash emission starting signal to initiate a flash output, a flash emission stopping signal indicative of a predetermined amount of light from said flash being received, and an exposure data signal indicative of exposure conditions;
   estimate reference signal generating means, connected to said automatic exposure controlling means, for producing an estimate reference signal indicative of a time that should elapse between said flash emission starting signal and said flash emission stopping signal if a proper subject is exposed by said camera, based on said exposure data signal and said flash emission starting signal from said automatic exposure controlling means;
   quality estimating means, connected to said automatic exposure controlling means and said estimate reference signal generating means, for determining whether said flash emission stopping signal from said automatic exposure controlling means is produced within a predetermined time threshold of said estimate reference signal and producing an estimating signal indicative thereof, thereby estimating if a proper subject is exposed by said camera; and
   estimation indicating means connected to said quality estimating means, for indicating said estimation result on the basis of the estimating signal emitted from said quality estimating means.

2. A retinal camera according to claim 1 wherein said estimation indicating means includes therein a lamp for indicating that the photographing result is good and a buzzer for indicating that the photographing result is not good.

3. A retinal camera according to claim 2 wherein said lamp indicates said good result by flickering.

4. A retinal camera according to claim 1 further comprising a keyboard for inputting said exposure data signal.

5. A camera as in claim 1 wherein said automatic exposure controlling means includes an integrator for integrating an amount of light received and producing said flash emission stopping signal when said predetermined amount of light is received.

6. A camera as in claim 1 wherein said quality estimating means estimates an erroneous exposure when said flash emission stopping signal is produced less than a predetermined time threshold before said estimate reference signal.

7. A camera as in claim 1 wherein said quality estimating means estimates an erroneous exposure when said flash emission stopping signal is produced more than a predetermined time threshold after said estimate reference signal.

8. A camera as in claim 7 wherein said quality estimating means also estimates an erroneous exposure when said flash emission stopping signal is produced more than a predetermined time threshold before said estimate reference signal.

9. A retinal camera for photographing an object that is to be irradiated by a photographic flash, comprising:

light receiving means for receiving a reflection of a flash from said object to be photographed and producing an output indicative thereof;

automatic exposure controlling means, connected to said light receiving means, and including:

(a) integrator means for integrating the output from said light receiving means, and (b) means for determining rate of rising of an output of said integrator means at a predetermined time point, said automatic exposure controlling means for emitting a flash emission starting signal to initiate said flash, and for producing a flash emission stopping signal when said output of said integrator means reaches a predetermined level and an exposure data signal;

estimate reference signal generating means, connected to said automatic exposure controlling means, for producing an estimate reference signal indicative of a time beginning at said flash emission starting signal, and after which said flash emission stopping signal should be received, if a proper subject is exposed by said camera, as a reference for estimating the quality of a photographing result, and based on said exposure data signal and said flash emission starting signal from said automatic exposure controlling means, and for producing signals indicative of an upper limit value and a lower limit value indicative of a permissible range around said estimate reference signal;

quality estimating means, connected to said automatic exposure controlling means and said estimate reference signal generating means, for comparing the integrated output from said integrator means with said two signals corresponding to said lower limit value and said upper limit value from said estimate reference signal generating means; and estimation indicating means, connected to said quality estimating means, for indicating an estimation result based on said estimating signal from said quality estimating means.

10. A retinal camera according to claim 9 further comprising keyboard means for inputting said exposure data signal.

11. A retinal camera according to claim 9 wherein said estimation indicating means includes therein a lamp for indicating that the photographing result is good and a buzzer for indicating that the photographing result is not good.

12. A retinal camera according to claim 11 wherein said lamp indicates said good result by flickering.

13. A camera as in claim 9 wherein said quality estimating means estimates an erroneous exposure when said flash emission stopping signal is produced less than a predetermined time threshold before said estimate reference signal.

14. A camera as in claim 9 wherein said quality estimating means also estimates an erroneous exposure when said flash emission stopping signal is produced more than a predetermined time threshold after said estimate reference signal.

15. A camera as in claim 14 wherein said quality estimating means also estimates an erroneous exposure when said flash emission stopping signal is produced more than a predetermined time threshold before said estimate reference signal.

* * * * *